(12) United States Patent
Howes, Jr. et al.

(10) Patent No.: US 9,829,475 B2
(45) Date of Patent: Nov. 28, 2017

(54) PPM POOL SENSOR

(71) Applicant: Ecolab USA Inc., St. Paul, MN (US)

(72) Inventors: Ronald Bruce Howes, Jr., Minneapolis, MN (US); Patrick Henry Kilawee, Hugo, MN (US); Leonard John Kadlec, Woodbury, MN (US)

(73) Assignee: Ecolab USA Inc., St. Paul, MN (US)

( * ) Notice: Subject to any disclaimer, the term of this patent is extended or adjusted under 35 U.S.C. 154(b) by 237 days.

(21) Appl. No.: 14/535,523

(22) Filed: Nov. 7, 2014

(65) Prior Publication Data

US 2016/0131608 A1     May 12, 2016

(51) Int. Cl.
    *G01N 27/07*    (2006.01)
    *G01N 33/18*    (2006.01)
    *G01N 27/49*    (2006.01)

(52) U.S. Cl.
    CPC ......... *G01N 33/182* (2013.01); *G01N 27/49* (2013.01)

(58) Field of Classification Search
    CPC ........ G01N 27/07; G01N 27/27; G01N 27/49; G01N 33/182; G01N 33/0031; G01N 33/1813; G01N 27/4162; H01C 10/025; G01L 1/20; H02K 44/085
    See application file for complete search history.

(56) References Cited

U.S. PATENT DOCUMENTS

| | | | |
|---|---|---|---|
| 2,851,655 A | 9/1958 | Haddad | |
| 3,959,087 A | 5/1976 | Morrow | |
| 4,033,830 A | 7/1977 | Fletcher, III | |
| 4,129,479 A | 12/1978 | Morrow | |
| 4,822,474 A | 4/1989 | Corrado | |
| 5,230,785 A | 7/1993 | Yager | |

(Continued)

FOREIGN PATENT DOCUMENTS

| | | |
|---|---|---|
| DE | 10029568 A1 | 7/2003 |
| EP | 0065166 A2 | 11/1982 |

(Continued)

OTHER PUBLICATIONS

U.S. Appl. No. 14/533,343, entitled: Sensor System and Method for Sensing Chlorine Concentration, filed Nov. 5, 2014, 28 pages.
International Search Report for PCT/US2015/057741, Date of Mailing: Feb. 10, 2016, 10 pages.

*Primary Examiner* — Son Le
(74) *Attorney, Agent, or Firm* — Fredrikson & Byron, P.A.

(57) ABSTRACT

A sensor including first and second electrodes can be used to determine the concentration of at least one chemical constituent in a fluid sample under test. The electrodes can be disposed in the fluid sample and a predetermined voltage can be applied to a first electrode. The voltage can cause a current to flow between the first and second electrodes through the sample, the current dependent on the concentration of the chemical constituent in the fluid sample. A sense resistor is coupled to the first electrode such that the current flowing between the electrodes flows through the sense resistor. A processor electrically isolated from the electrodes can receive data signals indicative of the voltage drop across the sense resistor and the voltage applied at the first electrode. The received signals can be used to determine the concentration of the constituent in the fluid sample.

20 Claims, 5 Drawing Sheets

(56) References Cited

U.S. PATENT DOCUMENTS

| | | | |
|---|---|---|---|
| 6,338,782 B1* | 1/2002 | Imamura | G01N 27/4067 204/424 |
| 7,100,427 B2 | 9/2006 | Kahn et al. | |
| 8,505,565 B2 | 8/2013 | Hin et al. | |
| 2001/0042692 A1 | 11/2001 | Gurry et al. | |
| 2003/0033848 A1* | 2/2003 | Peng | G01N 33/007 73/1.06 |
| 2004/0211731 A1 | 10/2004 | Ferguson et al. | |
| 2007/0158274 A1 | 7/2007 | King | |
| 2009/0201032 A1 | 8/2009 | Burdett et al. | |
| 2011/0308645 A1 | 12/2011 | Thai et al. | |
| 2013/0233728 A1* | 9/2013 | Day | G01N 27/4075 205/780.5 |
| 2014/0026971 A1* | 1/2014 | Roach | C25B 15/08 137/3 |
| 2014/0326680 A1 | 11/2014 | Mastio | |

FOREIGN PATENT DOCUMENTS

| | | |
|---|---|---|
| EP | 0065167 A2 | 11/1982 |
| FR | 2947634 A1 | 1/2011 |
| JP | 2007117882 A | 5/2007 |
| MX | 2009010771 A | 4/2011 |
| WO | 9924369 A2 | 5/1999 |
| WO | 0238507 A1 | 5/2002 |
| WO | 2011003923 A1 | 1/2011 |
| WO | 2012112611 A2 | 8/2012 |

\* cited by examiner

PPM POOL SENSOR

TECHNICAL FIELD

This disclosure relates to concentration monitoring of a fluid sample, such as monitoring the concentration of chlorine in a pool or spa.

BACKGROUND

Dispensing systems for dosing certain substances (e.g., chlorine) in fluids (e.g., recreational water bodies such as pools, spas, water parks, and the like) often require sensing the concentration of the substance. One type of sensor for such applications is an Oxidation-Reduction Potential (ORP) sensor for monitoring levels of chlorine in recreational water bodies. ORP sensors measure the ability of a substance to act as an oxidizing or reducing agent. Chlorine is an oxidizing agent, and the presence of chlorine in fluids can therefore be indirectly measured by the ORP sensor. ORP sensors are widely used due to their lower cost. However, ORP sensors may have several disadvantages. For instance, ORP sensors can have a non-linear signal response to chlorine concentration in the range of chlorine concentrations typically used in recreational water bodies (e.g., 1 to 10 ppm). Also, high impedance characteristics of ORP sensors may be sensitive to external electrical noise (e.g., stray electrical currents), thereby reducing the accuracy of measurement. Moreover, ORP sensors typically do not directly sense chlorine concentration and rather sense oxidation reduction potential, which in turn can be affected by various parameters such as pH, temperature, and the presence of other chemical species in the fluid. As a result, ORP sensors may need a calibration procedure to measure the ORP sensor response to chlorine concentration in a given water body. ORP sensors therefore must be "hand tuned" according to the physical conditions (e.g., pH, temperature, etc.) prevalent in each water body where ORP sensors are used. Such calibration procedures can become unreliable over time due to changing conditions in the water body and may increase equipment and maintenance costs.

Another type of sensor for measuring concentration of certain substances (e.g., chlorine) in a fluid (e.g., water) is an amperometric sensor. Such amperometric sensors can measure concentration of an ion based on an electric current (or changes therein) flowing between a pair of electrodes. Unlike ORP sensors, amperometric sensors can have a linear signal response to chlorine concentration and low electrical impedance. As a result, there may not be significant electrical noise interference in amperometric sensors resulting in better accuracy of measurement than ORP sensors. Such sensors also have a simple construction and low cost. In addition, amperometric sensors generally have predictable responses from sensor to sensor, eliminating the need for high cost calibration procedures.

SUMMARY

Embodiments of the invention generally relate to a chemical monitoring system for a body of water, including sensors for use therein and methods for using the same. Exemplary systems can be amperometric sensors, and can include a processor, a first electrode electrically isolated from the processor, and an adjustable power supply configured to provide a predetermined voltage at the first electrode. The adjustable power supply can be electrically isolated from and in communication with the processor for maintaining the electrically isolated predetermined voltage at the first electrode. The sensor can further include a sense resistor connected in series between the first electrode and the adjustable power supply, and a second electrode.

In some examples, the first and second electrodes can be disposed in a fluid sample under test. The predetermined voltage applied to the first electrode can be such that it causes a current to flow from the first electrode through the fluid sample under test to the second electrode. The current can be provided from the adjustable power supply such that the current flows through the sense resistor as it travels toward the first electrode.

Sensors can include an analog-to-digital converter (ADC) in communication with and electrically isolated from the processor. The ADC can provide information to the processor regarding the voltage applied to the first electrode and the voltage drop across the sense resistor due to the current flowing therethrough. Exemplary information can include signals indicative of a voltage at a first side of the sense resistor, a voltage at a second side of the sense resistor, opposite the first, and the voltage at the first electrode. In some examples, the voltage at the first electrode is the same as or otherwise able to be determined from the voltage at one side of the sense resistor.

The processor can receive information from the ADC. The processor can control the adjustable power supply based on the determined voltage at the first electrode. Additionally, the processor can determine the voltage drop across the sense resistor, and determine the current flowing through the sense resistor based on the determined voltage drop. In some examples, the processor can use the detected current to determine the concentration of one or more chemical constituents in the fluid sample under test, such as chlorine or other oxidants. The electrical isolation between the processor and other sensor components (e.g., power supply, ADC) allows for the determination of the current flow between the electrodes while isolating the electronics from the electrical ground of the water body environment. Such isolation can prevent ground loops and stray currents which could be dangerous to people or equipment proximate the water body.

The sensor and/or the system can include one or more auxiliary sensors, such as temperature, pH, flow rate, turbidity, or other sensors, configured to provide auxiliary data to the processor. The processor can use the auxiliary data in addition to data regarding the current flowing through the first electrode to supplement the determination of the concentration of a constituent of the fluid sample.

BRIEF DESCRIPTION OF DRAWINGS

The following drawings are illustrative of particular embodiments of the present invention and therefore do not limit the scope of the invention. The drawings are not necessarily to scale (unless so stated) and are intended for use in conjunction with the explanations in the following detailed description. Embodiments of the invention will hereinafter be described in conjunction with the appended drawings, wherein like numerals denote like elements.

DETAILED DESCRIPTION

Figure 1:
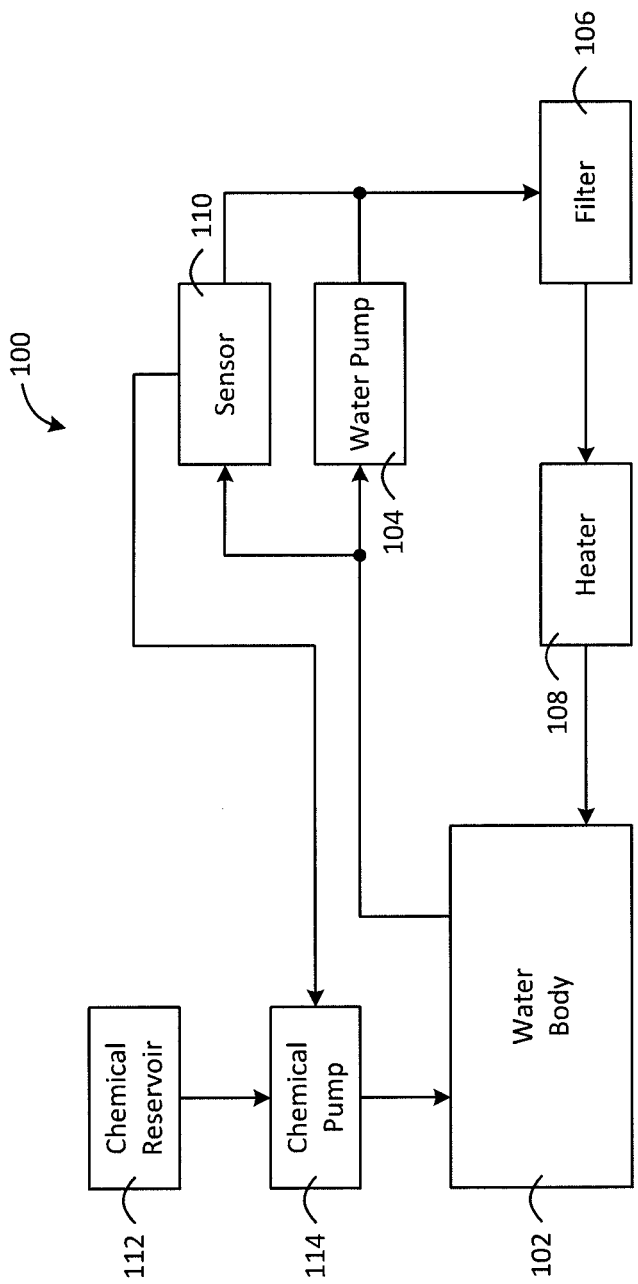
FIG. 1 is a block diagram of an exemplary system in which such a sensor can be implemented.

Aspects of the invention are directed toward a sensor for determining and/or controlling chemical levels in a body of water. FIG. 1 is a block diagram of an exemplary system in which such a sensor can be implemented. The system 100 of FIG. 1 includes a water body 102 such as a pool or spa which is intended to be treated. The system can include a water pump 104 for circulating water through a water circulation loop including various components of the system. For example, in the illustrated system 100, the water pump 104 can circulate water from the water body 102 through a filter 106 and a heater 108 before returning the water to the water body 102. Often, the water body 102 is treated with one or more chemicals, which can be stored in one or more chemical reservoirs 112 and incorporated to the water body 102 via one or more chemical pumps 114. Exemplary chemicals to be added to the water can include chlorine or acidic chemicals for maintaining a desired chemistry in the water body 102.

System 100 can include a sensor 110 configured to monitor one or more properties of the water in the water body. In some examples, the sensor or other system components or configurations can be such as described in U.S. patent application Ser. No. 14/533,343, filed Nov. 5, 2014, which is assigned to the assignee of the instant application, and which is hereby incorporated by reference in its entirety. In some embodiments, sensor 110 can be positioned in a loop with the water pump 104 so that the sensor 110 receives at least a portion of the water pumped by the pump 104. In some embodiments, the sensor 110 can be placed in series with the water pump 104. In some such embodiments, the sensor receives all of the fluid flowing through the water circulation loop. In the illustrated embodiment, the sensor 110 is positioned in parallel with the water pump 104, and is configured to receive only a portion of the pumped water. In various examples, the sensor 110 can be positioned in parallel to any part of the flow loop and receive a portion of the water that flows through the loop. Some systems can include valves to control the flow of fluid to the sensor 110 from the water circulation loop.

In some systems, the sensor can be in communication with one or more chemical pumps 114, which can be configured to dispense one or more corresponding chemicals from chemical reservoirs 112 into the water body 102. Accordingly, the sensor 110 can control the addition of one or more chemicals to the water body 102 based on one or more sensed parameters. For instance, in the event that the sensor 110 detects a level of a particular chemical (e.g., chlorine) below a desired level, the sensor 110 can cause the chemical pump 114 to dose the chemical from the chemical reservoir 112 into the water body 102.

In some examples, the sensor 110 can include an amperometric sensor. Amperometric sensors can generally be one of two types. In a first type, a passive galvanic amperometric sensor, a voltage is generated between dissimilar metals of two electrodes due to electrochemical action of oxidants in the water. The resulting voltage can be used to determine the level of oxidants. In some cases, passive galvanic sensors can have a limited measurement range, as the voltage can saturate under low or high concentration conditions. The second type of amperometric sensor is an active bias sensor. In an active bias sensor, a small voltage is applied to a first electrode which causes an electrical current to flow between the first and a second electrode. The current is indicative of the level of oxidants in the water. The active bias sensor can require very tight control over the applied bias, and can be sensitive to other parameters of the fluid, such as flow rate, temperature, pH, and the amount of total dissolved solid (TDS) in the fluid.

Embodiments of the present invention relate to an amperometric sensor configured to operate at least in active bias mode. As such, the sensor 110 of FIG. 1 can include an amperometric sensor. The amperometric sensor can include a first electrode for applying a voltage to a fluid sample, and a second electrode for receiving a resulting current from the applied voltage. In some embodiments, the first electrode comprises platinum or gold while the second electrode comprises copper, though a variety of appropriate materials can be used. The sensor can further include a power supply for providing a voltage to the first electrode, circuitry for measuring current flowing between the second electrodes as a result of the voltage applied to the first electrode, and a processor for controlling the voltage applied to the first electrode and determining the current flowing between the second electrodes. In some embodiments, the second electrode can be connected to a system ground in order to ground the current flowing thereto.

In some applications, for example in a pool or spa, it is desirable to electrically isolate components of the sensor from the water body environment common ground. Electrically isolating such components eliminate ground paths between various points in the circuitry of the sensor and the surrounding environment. This can help reduce stray electrical currents from being detected at the electrodes and falsely contributing to the signal. Additionally, a lack of isolation can result in ground loops that can be dangerous to people in or around the water body or the electrical components. Accordingly, systems can include electrical isolation between various components of the sensor. For example, the sensor can include electrical isolation between the processor and the power supply such that the power supply is isolated from the water body ground. Systems can further provide electrical isolation between the current sensing circuitry and the processor. Accordingly, the processor can be powered via traditional, non-isolated power while the circuitry and power supply interfacing with one or more electrodes in communication with the water body are isolated from water body ground.

Figure 2:
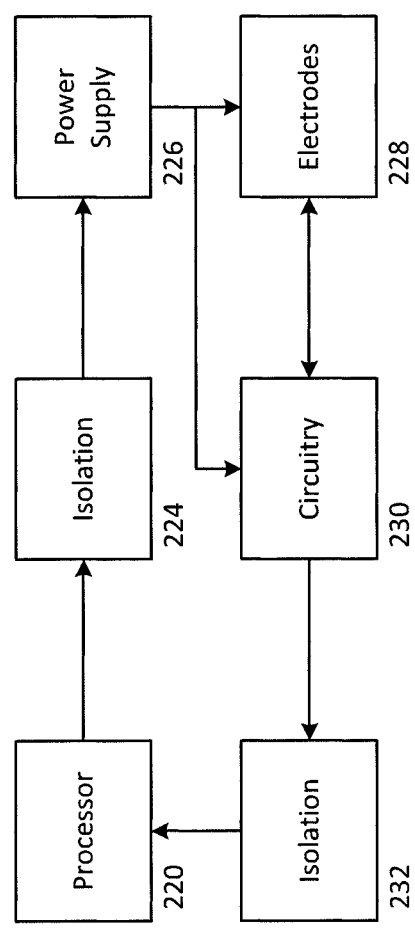
FIG. 2 is a schematic illustrating communication of components within an exemplary sensor.

FIG. 2 is a schematic illustrating communication of components within an exemplary sensor. The sensor of FIG. 2 includes a processor 220 in communication with a power supply 226 via isolation 224. The isolated power supply 226 can be in communication with one or both of one or more electrodes 228 and current sensing circuitry 230. That is, the power supply 226 can be configured to provide voltage to one or more electrodes 228 as desired, provide electricity to circuitry 230, or both. In some examples, the one or more electrodes 228 comprises a plurality of electrodes, and the power supply 226 provides a voltage to only a subset of the plurality of electrodes. In some such examples, one or more unpowered electrodes can be connected to an isolated ground. The current sensing circuitry 230 can interface with one or more electrodes 228 to receive signals indicative of the current flowing through the one or more electrodes 228. For instance, in some examples, the current sensing circuitry 230 can interface with a single electrode in order to receive signals indicative of the current flowing between the single electrode and a second electrode, which can be coupled to an isolated ground. In some embodiments, power is provided to one or more electrodes 228 by power supply 226 via circuitry 230. The circuitry 230 can communicate information back to the processor 220 via isolation 232. In some embodiments, isolation 224 and/or 232 can be achieved via transformers, optical isolators, photovoltaic isolators, capacitive isolators, or any other appropriate isolating communication.

In some arrangements, chlorine and/or other chemicals in the water being analyzed can interact with the first electrode and cause the variations in the voltage applied to the sample. However, in at least some operations, a constant bias voltage is desired. Accordingly, in some embodiments, the processor 220 can operate in conjunction with the isolation 224 and/or power supply 226 to provide a constant bias voltage at the first electrode. In an exemplary embodiment, the processor 220 receives a signal indicative of the applied bias voltage at the first electrode and provides an output to one or both of isolation 224 and power supply 226 to adjust the bias voltage applied to the first electrode in response to any detected deviation.

In some amperometric configurations, circuitry such as 230 can include a current-to-voltage converter circuit for determining current flowing between the first and second electrodes. Some such configurations include an operational amplifier with the first electrode coupled to the inverting input and the output coupled to the inverting input via a feedback resistor. In such a configuration, the inverting nature of the current-to-voltage converter results in a negative output. In order to operate the operational amplifier as such, both positive and negative power is required. Accordingly, the sensor requires both positive and negative power for simultaneous operational amplifier and bias electrode operation. Some such configurations require two power supplies for providing both positive and negative power. This can become costly and/or complex if electrical isolation of the current sensing circuitry is desired as previously discussed.

In some embodiments, circuitry 230 is configured to require only a single isolated power supply for operating the sensor. In some such embodiments, circuitry 230 can include a sense resistor coupled to the first electrode such that current flowing between the first and second electrodes similarly flows through the sense resistor. For instance, current can flow from the power supply 226, through a sense resistor to the first electrode, and through the sample to the second electrode, which may be coupled to an isolated ground. The voltage drop across the sense resistor can be used to determine the current flowing therethrough, and accordingly, the current flowing between the first and second electrodes. In some examples, the sense resistor can be a high precision resistor. For instance, the sense resistor can have a resistance of 40.2 kilohms±0.1%. Various resistances can be used with the same or different accuracy tolerance. In some embodiments, the resistance of the sense resistor can range from approximately 1 kilohm to 500 kilohms. In some examples, the value of the resistance can be stored in memory accessible by the processor 220 for use in various calculations and processes.

Circuitry 230 can include one or more amplifiers (e.g., operational amplifiers) for measuring the voltage drop across the sense resistor. In some examples, amplifiers can be configured as unity gain or other non-inverting amplifiers, and accordingly do not require dual polarity power applied thereto. Circuitry 230 can include a comparison circuit including a pair of such amplifiers to determine the voltage drop across the sense resistor in order to determine the current flowing therethrough. The circuitry can further include a comparison power supply for powering components of the comparison circuit (e.g., amplifiers). In some examples, the comparison power supply includes a single unipolar power supply. In some such embodiments, the amplifiers can be powered by the output of the unipolar power supply and an isolated ground. Accordingly, measurements of the voltage, and therefore the current, can be performed without requiring dual polarity isolated power.

Figure 3:
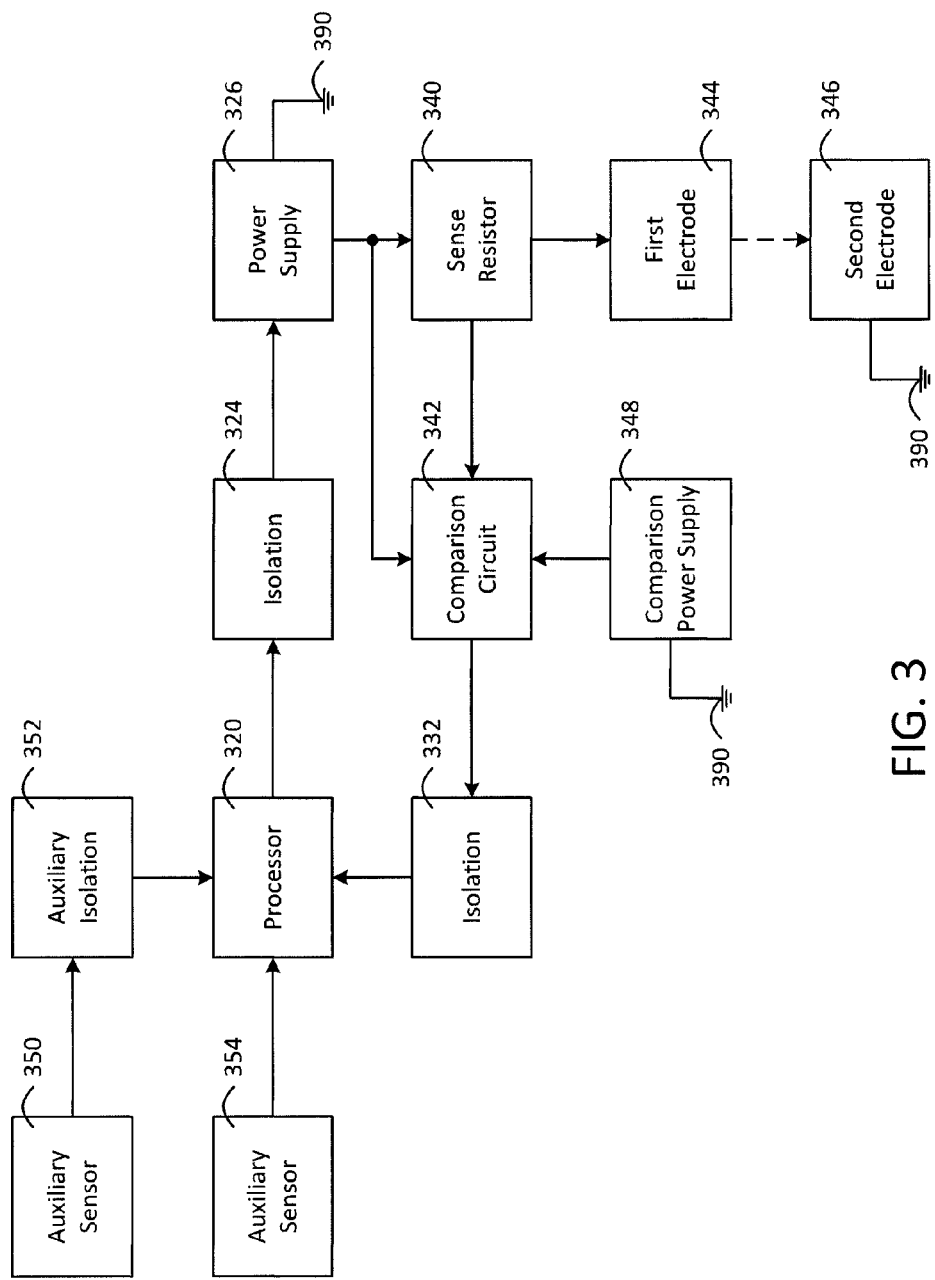
FIG. 3 is an expanded block diagram illustrating an exemplary sensor including a sense resistor and a comparison circuit.

FIG. 3 is an expanded block diagram illustrating an exemplary sensor including a sense resistor and a comparison circuit. The schematic of FIG. 3 includes a first electrode 344 and a second electrode 346. During operation, the electrodes can be disposed in a fluid sample under test. The sensor of FIG. 3 further includes a processor 320 coupled to an isolated power supply 326 via isolation 324. In some instances, isolation 324 can include an opto-isolator. The power supply 326 can provide isolated a voltage to a first electrode 344 relative to an isolated ground 390. The voltage at the first electrode 344 can cause a current to flow from the power supply 236 and between the first electrode 344 and a second electrode 346 through the fluid sample under test as illustrated by a broken line. The second electrode 346 can be coupled to an isolated ground 390. In some examples, the power supply 326 can be coupled to the first electrode 344 via a sense resistor 340 such that current flowing through the first electrode 344 to the second electrode flows through the sense resistor 340, creating a voltage drop across the resistor. Thus, in some such systems, a voltage applied to the first electrode 344 can result in a current flowing from the power supply 326 through the sense resistor 340 to the first electrode, through the fluid sample under test, and to ground via the second electrode.

In some examples, the power supply 326 can be configured to provide electrical power to a comparison circuit 342. The comparison circuit 342 can be configured to measure or otherwise output one or more signals representative of the voltage drop across the sense resistor 340. In some examples, the comparison circuit 342 can include a pair of amplifiers. The amplifiers can be positioned relative to the sense resistor 340 in order to collectively produce an output indicative of the voltage drop across the sense resistor 340. For example, the amplifiers can be configured as unity gain amplifiers having respective inputs on either side of the sense resistor 340. In such a configuration, the difference between the outputs of the respective amplifiers is representative of the voltage drop across the sense resistor 340. Additionally, such a configuration can be constructed using non-inverting amplifiers, and therefore does not require dual polarity power for operating the amplifiers. Instead, the amplifiers can be powered by a single unipolar isolated power supply and an isolated ground. In some examples, isolated power for powering the operational amplifiers can be provided by one or more isolating elements, including opto-isolators or transformers (e.g., DC-DC converters). In some embodiments, isolated power for powering the operational amplifiers can be provided from the same or different isolating elements providing isolating between the processor and other components (e.g., isolation 324, 332).

As previously discussed, in some examples, the system can include a comparison power supply 348 for providing electrical power to the comparison circuit. For instance, the comparison circuit can include one or more amplifiers requiring electrical power for operation. For reasons presented above, the comparison circuit can include non-inverting amplifiers, and accordingly do not require power of opposite polarities for proper operation. As such, the comparison power supply 348 can include a single unipolar power supply. For example, amplifiers in the comparison circuit 342 can receive power from the unipolar power supply with reference to isolated ground 390.

The comparison circuit 342 can output one or more signals representative of the current flowing through the sense resistor 340. For instance, the output can include a voltage drop across the sense resistor 340 as measured by the comparison circuit 342, or measurements representative of the voltage on each side of the sense resistor 340 from which the voltage drop can be calculated. In some examples, the comparison circuit 342 can include an analog-to-digital converter for (ADC) outputting one or more digital signals representative of the current flowing through the sense resistor 340. The output of the comparison circuit 342 can be received by the processor 320 from which the voltage drop across the sense resistor 340 can be determined. To maintain electrical isolation of the circuitry, the comparison circuit 342 can output a signal to the processor 320 via isolation 332. In some examples, isolation 332 can include optical isolation (e.g., comprise one or more opto-isolators). Accordingly, in some examples, the processor 320 can receive one or more digital signals representative of the current flowing through the sense resistor 340, the one or more digital signals being electrically isolated from the comparison circuit 342 and the sense resistor 340.

The processor 320 can determine the current flowing through the sense resistor 340 based on the one or more received signals from the comparison circuit 342. In some examples, the processor 320 receives a value of the voltage drop across the sense resistor 340 and calculates the current flowing through the sense resistor 340 based on the received voltage. In other examples, the processor receives data indicative of the voltage on either side of the sense resistor 340, calculates the voltage drop across the sense resistor 340, and determines the current flowing therethrough. In some embodiments, the processor 320 is configured to determine the concentration of one or more constituents in the fluid sample under test based on the current flowing through the sense resistor 340. For instance, in some examples, the processor 320 is configured to at least determine the chlorine concentration of the fluid sample under test.

In some embodiments, the processor 320 can control and/or monitor an active bias voltage applied to the first electrode 344. For instance, the comparison circuit can detect a voltage from the side of the sense resistor 340 coupled to the first electrode 344, thereby detecting the voltage at the first electrode 344. In such an embodiment, the processor 320 can receive an output from the comparison circuit 342 representative of the voltage applied to the first electrode 344. In some examples, the processor 320 can determine the chlorine concentration of the fluid sample based on the applied voltage at the first electrode 344 and the current flowing through the sense resistor 340. In an exemplary embodiment, the processor 320 receives outputs indicative of the voltage on each side of the sense resistor 340, wherein one such output is further indicative of the voltage applied to the first electrode 344. The processor 320 can utilize such outputs to determine the current flowing through the sense resistor 340 and the chlorine concentration of the fluid sample under test.

Some systems can include one or more auxiliary sensors for determining one or more additional parameters of the fluid sample under test. Exemplary auxiliary sensors can include, but are not limited to, temperature sensors, pH sensors, turbidity sensors, conductivity sensors, flow meters, or any appropriate sensor for determining a parameter of the fluid sample. The processor 320 can receive auxiliary data from one or more auxiliary sensors, and in some instances, can use the auxiliary data to determine a property of the fluid sample. For example, auxiliary data can supplement other data (e.g., the current through the sense resistor 340 or the voltage at the first electrode 344) in calculating the concentration of one or more constituents (e.g., chlorine) in the fluid sample.

In various embodiments, auxiliary sensors can be in communication with the processor 320. In some instances, auxiliary sensors can be electrically coupled to the processor. Additionally or alternatively, auxiliary sensors can be in communication with but electrically isolated from the processor 320. In general, any combination of electrically isolated and electrical coupled auxiliary sensors can be used. In the illustrated embodiment of FIG. 3, the sensor includes an auxiliary sensor 354 is shown in electrical communication with processor 320. Auxiliary sensor 354 can provide auxiliary data directly to the processor 320. The sensor further includes an auxiliary sensor 350 coupled to the processor 320 vial auxiliary isolation 352. Auxiliary isolation 352 can include any appropriate isolation components, including transformers, opto-isolators, and the like. For example, auxiliary sensor 350 can communicate auxiliary data to the processor 320 via an optically isolated communication device. In some instances, one or more auxiliary sensors are electrically powered. Isolated auxiliary sensors (e.g., 350) can be powered via a galvanically isolated power supply, while auxiliary sensors electrically coupled to the processor can be powered by an un-isolated power supply. In an exemplary embodiment, the sensor can include a pH probe in communication with and isolated from the processor, and a conductivity probe and a temperature probe in un-isolated communication with the processor. In general, isolated auxiliary components can be isolated from the processor or other un-isolated components by the same or different isolators as are used to isolate the electrodes from the processor.

Figure 4:
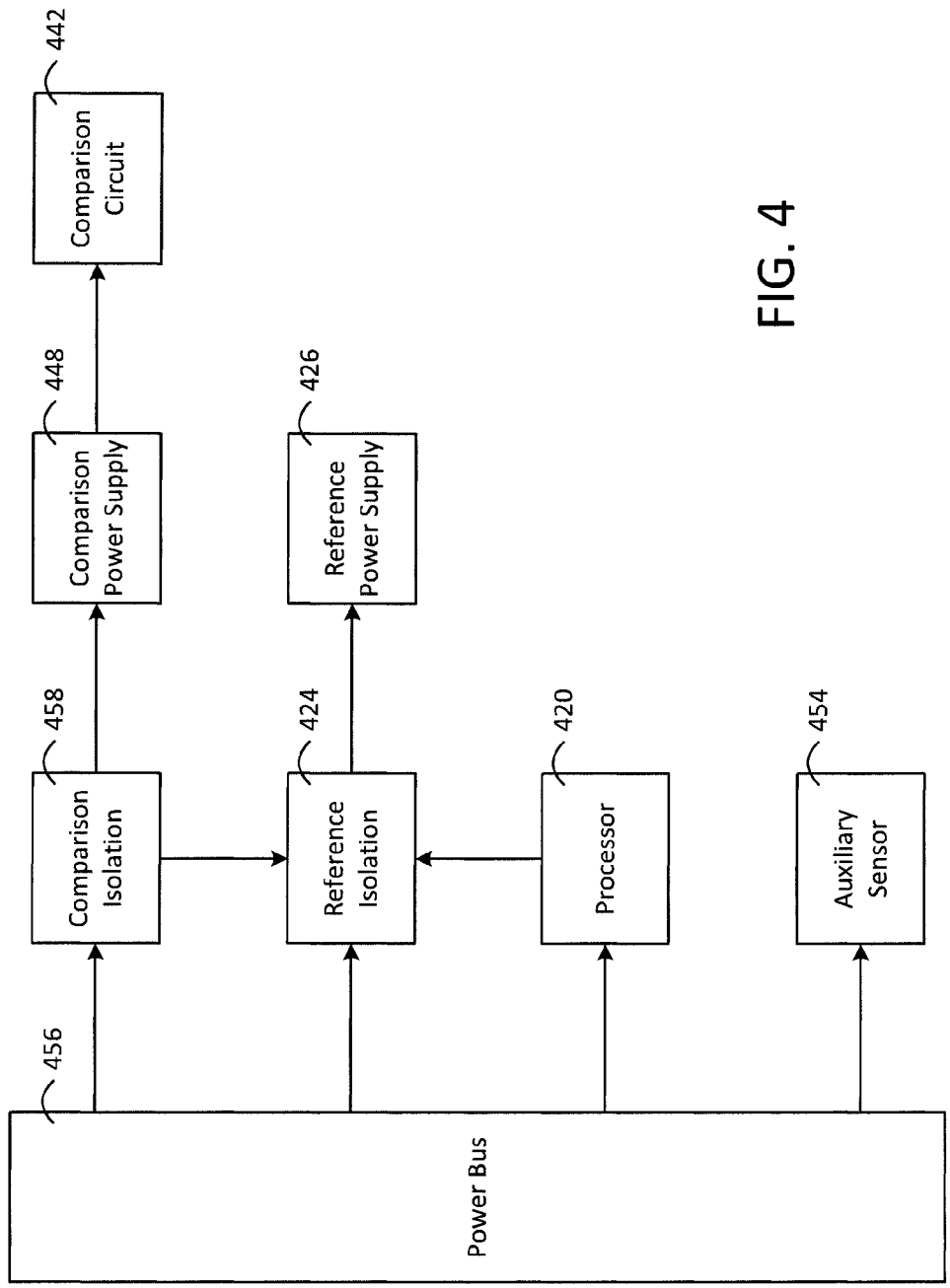
FIG. 4 is a schematic diagram illustrating exemplary power application in a sensor such as that shown in FIG. 3.

FIG. 4 is a schematic diagram illustrating exemplary power application in a sensor such as that shown in FIG. 3. The exemplary sensor of FIG. 4 includes a power bus 456 configured to provide electrical power to any number of components of the sensor. In some examples, power bus 456 is configured to output a constant voltage to each of the various components. In some examples, the power bus 456 provides 3.3 V relative to an un-isolated system ground, though any appropriate voltage can be used. In the illustrated example, the power bus 456 is configured to provide electrical power to a comparison circuit 442 via comparison isolation 458 and a comparison power supply 448. In some such examples, the power bus 456 provides un-isolated power to comparison isolation 458, which can provide isolated power to the comparison circuit 442 via the comparison power supply. In some instances, the comparison isolation 458 includes the functionality of the comparison power supply 448 and outputs power directly to the comparison circuit 442. In some examples, the comparison isolation 458 comprises a DC-DC converter.

The power bus 456 can provide power to reference isolation 424 configured to provide isolated power to a reference power supply 426. Reference power supply 426 can function similarly to power supply 326 of FIG. 3. The reference power supply 426 can provide power to the sense resistor and portions of the comparison circuit. Similarly as the comparison isolation 458, the reference isolation 424 can assume the functionality of the reference power supply 426 and provide electrical power directly to components of the system such as the sense resistor. In some embodiments, the reference isolation 424 can receive signals or power from one or both of the comparison isolation 458 and the processor 420. For instance, in some examples, reference isolation 424 requires power for operation, which can be provided from the comparison isolation 458.

In some examples, the processor 420 can provide a signal to the reference isolation 424 regarding the amount of power provided from the reference power supply 426. For instance, reference isolation 424 can include an opto-isolator powered by isolated power from the comparison isolation 458. The opto-isolator can be powered at an input (e.g., an anode and a cathode of a diode) by power from the power bus 456 and a signal from the processor 420, allowing processor 420 to control power provided from the reference isolation 424 (e.g., via a duty cycle). In the illustrated embodiment, the power bus 456 is configured to provide electrical power to processor 420. Power from the power bus 456 can be used to power the processor 420 or to provide a reference signal thereto.

In the illustrated embodiment, the power bus 456 provides power to an auxiliary sensor 454. Auxiliary sensor 454 can include any of, for example, temperature sensors, pH sensors, flow sensors, turbidity sensors, or any other appropriate sensor for determining properties of a fluid sample. In some examples, the power bus 456 can provide power to an auxiliary sensor via an isolating element so that the auxiliary sensor can be electrically isolated from the system ground. In other examples, auxiliary sensor 454 can be powered directly by the power bus 456.

It will be appreciated that, while shown as providing power to each of several components in FIG. 4, in various embodiments, power bus 456 can provide power to any subset of such devices. In some instances, one or more power buses can combine to provide electrical power to such components. One or more power buses can be configured to provide the same or different voltages to associated components electrically coupled thereto. In addition, FIG. 4 is intended to show particular instances of communication and coupled components according to some embodiments. Accordingly, various components shown in FIG. 4 may be coupled to other shown components without an illustrated connection between the two being shown in FIG. 4. In general, the arrangement illustrated in FIG. 4 is exemplary according to various embodiments of the sensor, and it will be appreciated that other arrangements and embodiments are possible.

Figure 5:
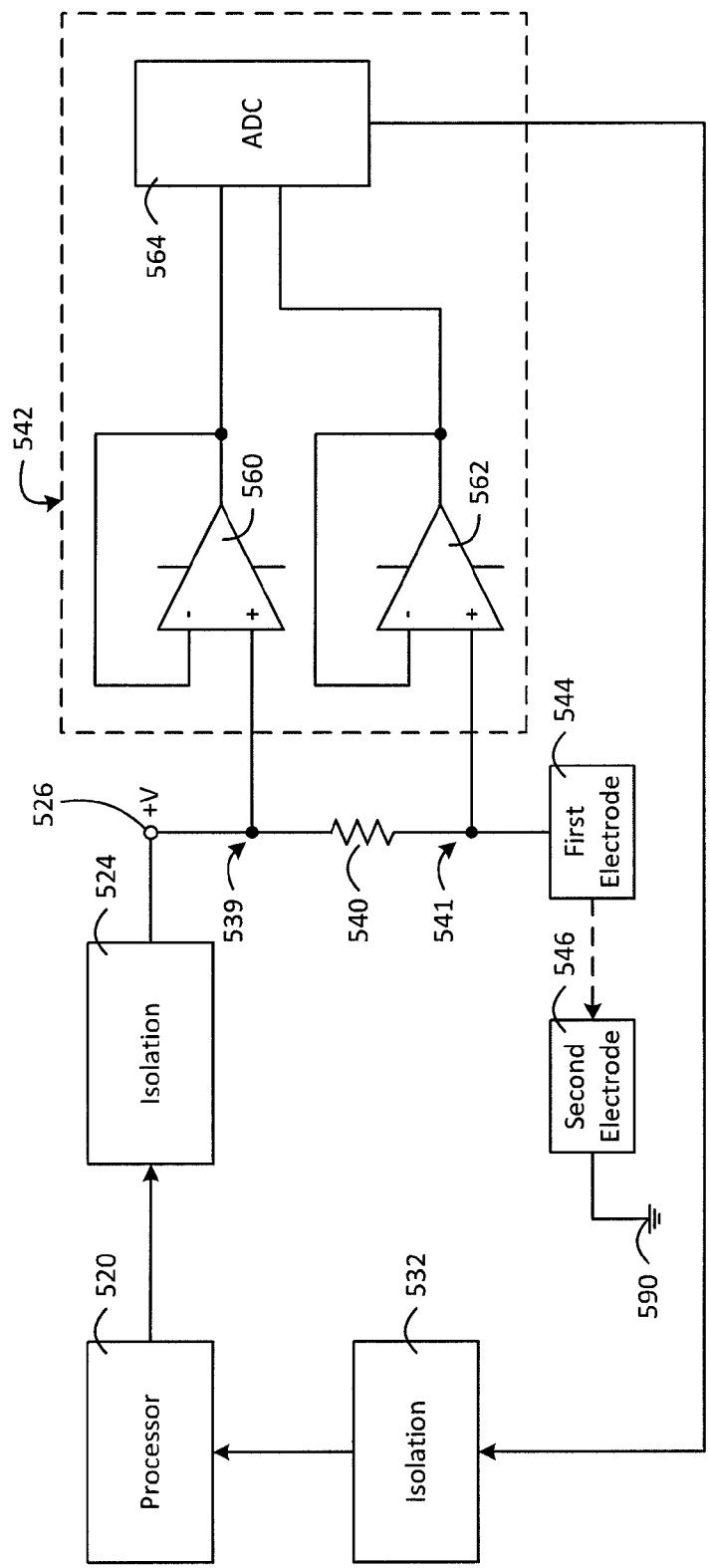
FIG. 5 is an exemplary schematic diagram illustrating communication between a processor, electrodes, and a comparison circuit.

FIG. 5 is an exemplary schematic diagram illustrating communication between a processor, electrodes, and a comparison circuit. FIG. 5 shows a processor 520 coupled through isolation 524 to a sense resistor 540. The sense resistor 540 is coupled on its other side to a first electrode 544. Either side of the sense resistor 540 is in electrical communication with the non-inverting input of an operational amplifier 560, 562. In the illustrated embodiment, the amplifiers are configured as unity-gain amplifiers, though other sensors can have alternative amplifier configurations. For example, amplifiers can output an amplified signal not equal to its input. In some embodiments, various amplifications may be used in accordance with achieving an output within a desired range, for instance, an input range of the ADC 564. Amplifiers 560 and 562 can be configured to have the same or different amplifications. In an exemplary embodiment (not shown), the first amplifier 560 can be a unity gain amplifier while the second amplifier 562 has an output twice the magnitude of its input.

The output of each amplifier is electrically coupled to an analog-to-digital converter (ADC) 564. The ADC 564 can provide digital signals to the processor 520 representative of the voltage sensed on either side of the sense resistor 540. In the illustrated example, the ADC 564 is coupled to the processor 520 via isolation 532, enabling interaction between the processor 520 and the other components electrically coupled to the fluid sample while maintaining electrical isolation therebetween. While shown as outputting a single channel toward isolation 532 and processor 520, the ADC may output two or more data streams to the processor 520, for example separate signals representative of the voltage on either side of the sense resistor 540.

In the illustrated embodiment, the input of operational amplifier 562 is coupled to a first electrode 544 and also to one side of the sense resistor 540, with its output inputted to the ADC 564 for transmission to the processor 520 via isolation 532. Accordingly, processor 520 can receive data indicative of the voltage at the first electrode 544 in addition to data regarding the voltage at either side of the sense resistor 540. It should be noted that, while various components of the sensor are shown as being directly connected in the illustrative embodiment of FIG. 5, such components may have intervening components disposed therebetween, such as filters (high pass, low pass, band pass, etc.), voltage dividers, or other circuit components that will affect the circuit in a predictable way. In general, the term "coupled" as used herein refers to components that may be directly connected, or may have intervening components therebetween.

During operation, the first 544 and second 546 electrodes can be disposed in a fluid sample under test. The processor can cause a voltage (+V) to be applied at the top of the sense resistor 540. The voltage can be electrically isolated from the processor 520, for instance by isolation 524. In some embodiments, the voltage +V can represent an adjustable power supply 526 configured to provide an isolated voltage to the circuit and controlled by the processor 520. As discussed with regard to FIG. 4, in some examples, the output of isolation 524 can act as an adjustable power supply 526 providing a voltage to a first side 539 of the sense resistor 540. The application of voltage +V can result in a voltage at the first electrode 544, of which a representative signal can be detected by the processor 520 via the ADC 564 and isolation 532. In some embodiments, the processor 520 can adjust its output such that a predetermined voltage is present at the first electrode 544. Processor 520 can adjust the voltage at the first electrode, for example, by adjusting the duty cycle of an output to isolation 524. For instance, in some examples, isolation 524 can include an opto-isolator, and the processor 520 can adjust the duty cycle of its output to the opto-isolator in order to effect an adjustment of the voltage at the first electrode 544. The sensor can include filtering circuits or other components configured to produce an output as a function of the duty cycle of a received input. As discussed, the voltage on the first electrode 544 can then be fed back to the processor 520 via, for example, ADC 564 and isolation 532.

The voltage on the first electrode 544 can cause a current to flow from the power supply at 526 through the sense resistor 540, the first electrode, through the fluid sample under test, and to the second electrode 546 where it reaches an isolated ground 590. The flowing current can cause a voltage drop across the sense resistor 540, and resultantly, affect the voltage at the first electrode 544. In some embodiments, the processor 520 monitors this change in the voltage at the first electrode 544 and adjusts its output to adjust the voltage at the first electrode 544. Accordingly, the processor 520 can maintain tight control over the voltage at the first electrode and adjust for any deviations to maintain a constant predetermined voltage.

As described, the voltage maintained at the first electrode 544 can cause a current to flow from the power supply 526 through the sample and to the isolated ground 590, resulting in a current flow through the sense resistor 540. The current flow through the sense resistor 540 creates a voltage drop across the sense resistor 540. In the illustrated example, the voltage at a first side 539 of the sense resistor 540 can be applied to the non-inverting input of operational amplifier 560, which can output a first voltage signal to the ADC 564. Similarly, the voltage at a second side 541 of the resistor 540 can be applied to the non-inverting input of operational amplifier 562, which can output a second voltage signal to the ADC 564.

The ADC 564 can receive the first and second voltages from operational amplifiers 560 and 562, respectively and output one or more signals to the processor 520 (via isolation 532) representative of the first and second voltages or the difference therebetween. In some examples, the ADC 564 outputs a first digital signal representative of the first voltage and a second digital signal representative of the second voltage. The digital signals can be received by the processor 520 via isolation 532. In various embodiments, the first and second digital signals can include the true values of the voltage at either side of the sense resistor 540. In alternative embodiments, one or both of the first and second digital signals can include a value that is a known multiple of one or both of the voltages on either side of the sense resistor 540. For instance, if amplifier 562 is configured with a gain of 2, the second digital signal from the ADC 564 can include a value that is double the value of the voltage at the second side 541 of the sense resistor 540. The processor 520 can be programmed with data regarding the amplification of the amplifiers 560 and 562, and can calculate the true voltage drop across the sense resistor 540 accordingly. In general, the processor can receive a signal representative of the difference between the first and second voltages, or can receive separate signals representative of the first and second voltages from which the processor can determine the difference between the first and second voltages.

In general, the sensor can include a comparison circuit 542 configured to determine and output one or more signals representative of the voltage drop across the sense resistor 540. In the illustrated embodiment, the comparison circuit 542 includes operational amplifiers 560 and 562 and ADC 564. The exemplary comparison circuit 542 receives the voltage from either side of the sense resistor 540 and communicates one or more signals to the processor (via isolation 532) indicative of the voltage drop across the sense resistor 540. In various embodiments, the comparison circuit performs a comparison of the voltage values, while in other embodiments, the comparison circuit outputs signals to be compared in order to determine the voltage drop across the sense resistor 540.

In the illustrated embodiment, the first electrode 544 is coupled to the second side 541 of the sense resistor 540. As such, in accordance with some embodiments, the processor 520 operates to maintain a constant voltage at the first electrode 544 and therefore at the second side 541 of the sense resistor 540. In the illustrated embodiment, maintaining a constant voltage at the second side 541 of the sense resistor 540 results in a constant voltage at the output of operational amplifier 562. Accordingly, in some such embodiments, only the output of operational amplifier 560 varies in response to the current flowing through the sense resistor 540, and the voltage drop across the sense resistor 540 is represented by the variation of the output of operational amplifier 560 with respect to the fixed output of operational amplifier 562.

In some such embodiments, voltage at the first electrode 544 is the same as the voltage at the second side 541 of the sense resistor 540, and can be determined from the output from operational amplifier 562. Such systems can require fewer isolating connections and ADC 564 inputs between the circuit and the processor 520, as well as fewer processor 520 inputs when compared to systems in which a first electrode is independent of current sensing components. This is because the measurement of the voltage at the first electrode 544 can be simultaneously used as a measurement representative of the voltage on the second side 541 of the sense resistor 540. Accordingly, separate inputs to the ADC 564 and processor 520, and separate isolating elements or inputs are not necessary for such measurements as would be if the two voltages were independent of one another. Such a configuration can reduce the cost and complexity of the system The processor 520 can determine the voltage drop across the sense resistor 540 based on the received one or more signals from the ADC 564. From the voltage drop and a known resistance value of the sense resistor 540 (e.g., stored in a memory), the processor 520 can determine the current flowing through the sense resistor 540, and thus the current flowing in the fluid sample under test, using Ohm's law, for example. As described, the processor 520 also controls/determines the voltage applied to the fluid sample under test via the first electrode 544. Accordingly, in some examples, the processor can determine the concentration of one or more constituents of the fluid sample under test based on the voltage applied at the first electrode 544 and the resulting current flowing between the first 544 and second 546 electrodes through the sample. For example, the processor can use such data to determine the concentration of chlorine in the fluid sample under test. In some examples, the processor can determine the concentration to a parts-per-million (ppm) accuracy.

As described previously, in some systems or sensors, the processor (e.g., 520) can receive auxiliary data from one or more auxiliary sensors. Such auxiliary sensor can include any combination of, but are not limited to, pH sensors, temperature sensors, conductivity sensors, turbidity sensors, flow sensors, and other sensors capable of providing auxiliary information regarding the fluid sample under test. In some embodiments, the processor can use auxiliary data from one or more auxiliary sensors as supplementary data to determine the concentration of the constituent in the fluid sample under test. For example, the processor can receive auxiliary data and combine the received auxiliary data with the current flowing through the sense resistor to determine the concentration of chlorine in the fluid sample under test. In various embodiments, the processor can further use auxiliary data to determine other parameters regarding the fluid sample under test.

Referring back to FIG. 1, the sensor 110 can be in communication with, for example, a chemical pump 114 configured to dose a chemical from a chemical reservoir 112 into the water body 102. In some examples, the sensor 110 can trigger one or more chemical pumps (e.g., 114) to dose one or more chemicals into the water body 102 based on data received by the processor. For instance, the sensor 110 can compare the determined concentration of chlorine in the fluid sample taken from the water body 102 to a threshold, and, in the event that the chlorine concentration is below the threshold, the sensor can cause a chemical pump configured to dose a chlorine-sourcing chemical into the water body. Chlorine-sourcing chemicals are generally known and can include, for example, calcium-hypochlorite or liquid bleach.

In some examples, the sensor can cause a chemical pump (e.g., 114) to dose a chemical into the water body 102 based on auxiliary data. For instance, in the event that an auxiliary pH sensor determines the pH is above a predetermined threshold, the sensor can cause a chemical pump to add an acidic or other pH-lowering chemical such as muriatic acid to reduce the pH value of the fluid in the water body 102. Various pH-lowering chemicals such as acids can be diluted to various degrees for effecting an appropriate pH change in the water body 102. Conversely, if the determined pH is below a predetermined threshold, the sensor can trigger a chemical pump to add a pH-raising chemical, for example, sodium carbonate. In various embodiments, the sensor 110 can further be in communication with the water pump 104 or the heater 108 to adjust operation in response to detected auxiliary data such as water flow rate or temperature.

In some embodiments, the sensor can actively monitor a fluid sample under test (e.g., water from the water body 102) to determine the concentration of a constituent such as chlorine in substantially real time. Any one or combination of the chlorine concentration and other received auxiliary data can be used to determine when and to what extent to add one or more chemicals to the water body 102 in order to maintain appropriate parameters of the fluid therein, such as chlorine concentration, pH, etc. The active and accurate determination of such parameters allows for real-time and tight control of parameters of the fluid in the water body 102, such as the chlorine concentration, pH, or other desired parameter. Such real-time control can reduce or eliminate overshoot, overcorrection, or undercorrection present in less precise systems.

Various embodiments of systems and sensor have been described. Such examples are non-limiting, and do not define or limit the scope of the invention in any way. Rather, these and other examples are within the scope of the following claims.

The invention claimed is:

1. A chemical monitoring system comprising a sensor, the sensor including:
   a processor;
   a first electrode electrically isolated from the processor;
   an adjustable power supply electrically isolated from and in communication with the processor and configured to provide a predetermined voltage at the first electrode;
   a second electrode;
   a sense resistor connected in series between the first electrode and the adjustable power supply;
   an analog-to-digital converter (ADC) in communication with and electrically isolated from the processor, and configured to provide information to the processor regarding (i) the voltage at the first electrode and (ii) the voltage drop across the sense resistor; wherein
   the processor receives the information from the ADC regarding the voltage on the first electrode, determines the voltage at the first electrode, and controls the adjustable power supply based on the determined voltage at the first electrode; and
   the processor receives the information from the ADC regarding the voltage drop across the sense resistor, determines the voltage drop across the sense resistor, and, based on the determined voltage drop across the sense resistor, determines the current flowing through the sense resistor.

2. The system of claim 1, wherein the processor is configured to determine the chlorine concentration in a fluid sample in which the first and second electrodes are inserted based on the current flowing through the sense resistor and the voltage applied to the first electrode.

3. The system of claim 2, further comprising at least one auxiliary sensor in communication with the processor, and wherein the processor receives auxiliary data from the at least one auxiliary sensor and determining the chlorine concentration in the fluid sample is further based on the auxiliary data.

4. The system of claim 3, wherein the at least one auxiliary sensor comprises at least one of a temperature sensor, a pH sensor, and a flow meter.

5. The system of claim 3, wherein the at least one auxiliary sensor is powered by a galvanically isolated power source.

6. The system of claim 5, wherein the at least one auxiliary sensor is in communication with the processor via an optical communication.

7. The system of claim 2, wherein the adjustable power supply comprises the output of an isolation component, and wherein the adjustable power supply is adjusted by the processor adjusting the duty cycle of a signal applied to the isolation component.

8. The system of claim 7, wherein the isolation component comprises an opto-isolator.

9. The system of claim 2, wherein the sensor further comprises a first amplifier and a second amplifier, the first amplifier configured to output a signal to the ADC representative of the voltage on a first side of the sense resistor and the second amplifier configured to output a signal to the ADC representative of the voltage at a second side of the sense resistor, opposite the first.

10. The system of claim 9, wherein the first and second amplifiers are powered by a single isolated and unipolar power supply.

11. The system of claim 9, wherein an input of the second amplifier is coupled to the first electrode and the output of the second amplifier is coupled to the ADC such that the ADC receives signals representative of both the voltage at the second side of the sense resistor and the voltage at the first electrode.

12. The system of claim 2, further comprising
   a water body containing a volume of water;
   a water pump configured to circulate water from the water body through components of the system;
   a chemical reservoir containing a chemical; and
   a chemical pump configured to dose the chemical from the chemical reservoir to the water body; wherein
   the sensor is configured to receive at least a portion of the water pumped by the water pump.

13. The system of claim 12, wherein the chemical in the chemical reservoir is one of calcium-hypochlorite and liquid bleach, and wherein the sensor is in communication with the chemical pump and is configured to operate the chemical pump based on the detected level of chlorine in the fluid sample.

14. A system comprising:
   a processor;
   a first electrode and a second electrode disposed in a fluid sample;

a reference power supply configured to provide a predetermined voltage at the first electrode that is galvanically isolated from the processor;

a sense resistor having a first side coupled to the reference power supply and a second side, opposite the first, coupled to the first electrode;

a comparison circuit having a first input coupled to the first side of the sense resistor and a second input coupled to the second side of the sense resistor and the first electrode, and configured to output one or more signals to the processor indicative of the voltage drop across the sense resistor and the voltage provided at the first electrode; and a comparison power supply configured to provide electrical power to the comparison circuit; wherein the comparison power supply is a single, unipolar power supply; and the processor is configured to (i) adjust the voltage at provided by the reference power supply based on the one or more signals indicative of the voltage provided at the first electrode so that the voltage at the first electrode is the predetermined voltage, and (ii) determine the concentration of chlorine in the fluid sample based on the voltage drop across the sense resistor and the predetermined voltage provided to the first electrode.

15. The system of claim 14, further comprising
a power bus, the power bus being electrically coupled to the processor;
a reference isolating element providing isolated power between the power bus and the reference power supply; and
a comparison isolating element providing isolated power between the power bus and the comparison power supply.

16. The system of claim 15, wherein the reference isolating element comprises an opto-isolator.

17. The system of claim 16, wherein the processor is coupled to the opto-isolator, and wherein adjusting the voltage provided at the reference power supply comprises adjusting a duty cycle of the opto-isolator in response to the one or more signals indicative of the voltage provided at the first electrode in order to maintain the first electrode at the predetermined voltage.

18. The system of claim 15, wherein the comparison isolating element comprises a DC-DC converter.

19. The system of claim 18, wherein the comparison circuit comprises
a first amplifier coupled to the first side of the sense resistor and being powered by the comparison power supply; and
a second amplifier coupled to the second side of the sense resistor and being powered by the comparison power supply.

20. A method for determining the concentration of chlorine in a fluid sample, comprising:
directing the fluid sample to simultaneously contact a first electrode and a second electrode;
applying a first voltage to a first side of a sense resistor, the sense resistor having a second side opposite the first, the second side being coupled to the first electrode;
detecting a second voltage at the first electrode via a processor, the processor electrically isolated from the first electrode;
adjusting the first voltage based on the detected second voltage to achieve and maintain a predetermined voltage at the first electrode;
detecting a voltage drop across the sense resistor;
determining, from the detected voltage drop across the sense resistor, the amount of current flowing through the sense resistor; and
determining, from the determined amount of current flowing through the sense resistor and the second voltage, the concentration of chlorine in the fluid sample.

* * * * *